United States Patent
Blomqvist

(10) Patent No.: US 8,761,871 B2
(45) Date of Patent: Jun. 24, 2014

(54) MEDICAL DEVICE COMPRISING AN IMPEDANCE MEASUREMENT MEANS TO MEASURE VISCERAL FAT

(75) Inventor: Andreas Blomqvist, Spånga (SE)

(73) Assignee: St. Jude Medical, AB, Jarfalla (SE)

( * ) Notice: Subject to any disclaimer, the term of this patent is extended or adjusted under 35 U.S.C. 154(b) by 1235 days.

(21) Appl. No.: 12/442,744

(22) PCT Filed: Sep. 25, 2006

(86) PCT No.: PCT/SE2006/001082
§ 371 (c)(1),
(2), (4) Date: Mar. 25, 2009

(87) PCT Pub. No.: WO2008/039111
PCT Pub. Date: Apr. 3, 2008

(65) Prior Publication Data
US 2010/0100146 A1    Apr. 22, 2010

(51) Int. Cl.
*A61B 5/053*    (2006.01)
*A61N 1/365*    (2006.01)

(52) U.S. Cl.
USPC ................... 600/547; 607/2; 607/9

(58) Field of Classification Search
USPC ........................ 607/17, 40; 600/547
See application file for complete search history.

(56) References Cited

U.S. PATENT DOCUMENTS

| | | | |
|---|---|---|---|
| 4,919,136 A | 4/1990 | Alt | |
| 5,282,840 A * | 2/1994 | Hudrlik | 607/28 |
| 5,876,353 A | 3/1999 | Riff | |
| 6,473,640 B1 | 10/2002 | Erlebacher | |
| 6,539,310 B2 | 3/2003 | Shimomura | |
| 6,889,076 B2 * | 5/2005 | Cigaina | 600/547 |
| 2002/0156393 A1 | 10/2002 | Cigaina | |
| 2003/0216663 A1 * | 11/2003 | Jersey-Willuhn et al. | 600/547 |
| 2004/0077969 A1 * | 4/2004 | Onda et al. | 600/547 |
| 2004/0172080 A1 | 9/2004 | Stadler et al. | |
| 2005/0101875 A1 * | 5/2005 | Semler et al. | 600/509 |
| 2005/0107717 A1 * | 5/2005 | Yamamoto et al. | 600/547 |
| 2005/0192509 A1 | 9/2005 | Kodama et al. | |
| 2005/0283091 A1 | 12/2005 | Kink et al. | |
| 2006/0184060 A1 * | 8/2006 | Belalcazar et al. | 600/547 |
| 2006/0235327 A1 * | 10/2006 | Masuo et al. | 600/547 |
| 2007/0255334 A1 * | 11/2007 | Keimel et al. | 607/40 |

FOREIGN PATENT DOCUMENTS

WO    WO 0079255 A1 *  12/2000

* cited by examiner

*Primary Examiner* — Kennedy Schaetzle
*Assistant Examiner* — Erica Lee

(57) ABSTRACT

A medical device having an impedance measurement circuit connected to at least two intracorporeal measurement electrodes arranged to measure the impedance of tissue inside the body of a patient. The impedance measurement circuit is adapted to apply a measurement current/voltage signal to the electrodes to measure and calculate the impedance of the measurement tissue, and to apply the calculated impedance value to a storage unit. The stored impedance values are used, by an analysis unit, to measure the amount of visceral fat of the tissue object inside the body of the patient.

13 Claims, 1 Drawing Sheet

MEDICAL DEVICE COMPRISING AN IMPEDANCE MEASUREMENT MEANS TO MEASURE VISCERAL FAT

BACKGROUND OF THE INVENTION

1. Field of the Invention

The present invention relates to a medical device according to the preamble of the independent claim.

2. Description of the Prior Art

Generally it is of major importance to be able to isolate people who are more susceptible to heart disease from people who are not in the danger zone.

Separating these patients early means that there should be ample time to suggest means of reducing the dangerous fat, thus decreasing the risk of heart disease and hospitalization. It is well known that the amount of visceral fat can be reduced by appropriate diets and exercise, which means that human suffering will be decreased and the costs for public health care will be lowered.

In fact, it is not how fat a person is that decides whether or not he or she is in danger of attaining a heart disease—it is the location of the fat. This means that not only obviously obese people or people with a high body mass index (BMI) are in danger, but many other people, especially women, that are not identified as in the risk zone as well. Recent research results have shown that it is not the subcutaneous fat, but instead the visceral fat that is of importance when judging whether or not somebody is in the risk zone of heart disease. Visceral fat is the fat surrounding the organs.

By using e.g. magnetic resonance imaging (MRI) it may be possible to get an idea of how large deposits of visceral fat a patient has. There are, however, alternatives to this method.

In the following, some exemplary impedance measurement systems are disclosed, using external electrodes applied on the skin of a patient, and used to determine the amount of fat tissue or visceral fat of a subject.

United States Patent Application Publication No. 2005/0107717 discloses a method and device for calculating visceral fat of a subject by a bioimpedance method applied by measuring the electric impedance ratio between the longitudinal width of the abdomen and the transversal width of the abdomen of the subject. The measurements are performed via electrodes applied on the skin of the subject.

U.S. Pat. No. 6,539,310 relates to a body type determination apparatus for providing an easy-understandable representation of fat tissue and lean tissue, respectively occupying in a body constitution of a subject. This is achieved by entering body data and from a measured bioelectric impedance also obtained by external electrodes.

Implantable impedance measurement systems are e.g. used in connection with heart stimulating devices to detect, e.g. oedema in a patient's lungs, or to monitor the condition of a patient's body tissue.

U.S. Pat. No. 5,282,840 relates to multiple frequency impedance measurement system for monitoring the condition of a patient's body tissue. The device includes electrodes for contacting the tissue to be monitored, circuitry for generating electrical signals of at least two frequencies for application to the tissue and circuitry for monitoring the impedance of the tissue, at the frequencies applied. The measured impedance values may be employed to detect changes in tissue condition, such as those induced by ischemia and by drug therapies. A microprocessor may average the stored impedance values over a period of hours, days, weeks, or even months, compare the measured impedances at the two frequencies, in order to identify changes of the impedance values for improving the stimulation therapy.

U.S. Pat. No. 6,473,640 relates to an implantable device and method for long-term detection and monitoring of congestive heart failure. A signal generator is employed to generate an electrical signal which is monitored to obtain a single or dual frequency measurement that can independently measure systemic venous and pulmonary (lung) impedance.

U.S. Pat. No. 5,876,353 discloses the use of an impedance monitor using direct current (DC) impedance measurements in order to obtain measurements of transthoracic impedance and respiratory rate of a patient. The measurements are taken over a long term to obtain a long term average signal so that differences can be used to assess the amount of tissue oedema over the long term changing condition.

Also United States Patent Application Publication No. 2005/028091 primarily relates to an edema detector, generally referred to as a method and apparatus for determining conditions of a biological tissue. The relative amount of intracellular and extracellular liquid (water) is determined by applying an excitation signal at two frequencies chosen that one of the frequencies may let the measurement current pass the cell membranes of the tissue. The resulting signals from the measurements are then processed, e.g. by cross-correlation calculations, and the result may be used to detect changes with regard to the amount of oedema.

The investigations concerning this field of medicine have determined, as discussed above, that visceral fat in general, regardless of its position, is more dangerous than subcutaneous fat. The present invention is based upon the fact that fat has much higher impedance than other parts of the body. Blood has for example a resistivity of approximately 1.6 Ωm, whereas fat has a resistivity of approximately 25 Ωm, which is about 15 times higher than blood. This is partly because blood contains 70-75% water, and fat (which is hydrophobic) contains as little as 10-20% water. Furthermore, it is worth to mention that the tissue in the body is mostly resistive with currents applied with a frequency below approximately 10 kHz. Other parts of the body have the following approximate values for the resistivity: heart: 2.5 Ωm (longitudinal) and 5.6 Ωm (transversal), which gives a weighted mean value of ~4.6 Ωm; lungs 11-21 Ωm, ~15 Ωm (mean), and other tissue approximately 10 Ωm.

SUMMARY OF THE INVENTION

In view of the foregoing it is the object of the present invention to achieve an improved measurement device for measuring visceral fat.

Since it is well known that fat has different impedance than muscles and blood, the invention is based on the recognition that it is possible to monitor the level of visceral fat using bio impedance measured over suitable areas inside the body. This will, of course not, provide an exact quantity of the visceral fat, but if, for example, an initial diagnose is made by using other methods, the DC-level, or AC-level, of the bio impedance may be used to monitor changes. That has the advantage that it can be seen whether a treatment is having effect or not, or if a patient's health is deteriorating. The levels of difference in the amount of visceral fat between patients at high risk and low risk are high enough so that it may be detected. As an example, in women with metabolic syndrome (a condition that severely increases the risk of attaining a heart disease), the amount of visceral fat was 33% higher than in non-metabolic syndrome patients. This suggests that, with previously accumulated knowledge of bio impedance, this increase of visceral fat can be monitored in time and the physician can be alerted so that lives can be spared, and the quality of life increased.

The signal obtained from active measurements of bio impedance with, for instance, a pacemaker, can be split up into two separate parts, the AC- and the DC-impedance. Measurements of both the AC- and the DC-impedance may be of interest here, e.g. the DC-component contains information regarding how the impedance over a given volume changes over time.

Once the electrode leads are in the body, as is the case with a pacemaker, it is a matter of choosing the most appropriate configuration to measure the visceral fat. It is then important to create a current vector that passes through the layer of fat that is targeted.

DESCRIPTION OF THE PREFERRED EMBODIMENTS

Generally the impedance measurement is performed by applying a known current between two electrodes and then measure the voltage potential between the electrodes, the ratio between the voltage and corresponding current value is the impedance.

When performing AC-measurements, the impedance measurement means breaks down the measurement voltage into a real portion, which is in phase with the measurement current; and an imaginary portion, which is displaced 90 degrees relative to the measurement current phases. To accomplish this, a measurement pulse generator in the impedance measurement means is arranged to deliver a reference signal. The measurement voltage components obtained are directly proportional to the real portion Re(Z) and the imaginary portion Im(Z) of the impedance (Z=U/I) at a constant measurement current. From the real portion Re(Z) and the imaginary portion Im(Z) of the impedance the control means calculates the value of the impedance Z and the phase angle phi, in accordance with the following formula:

$$|Z|=sqr(Re^2(Z)+Im^2(Z))$$

$$phi=arctan\, Im(Z)/Re(Z)$$

Figure 3:
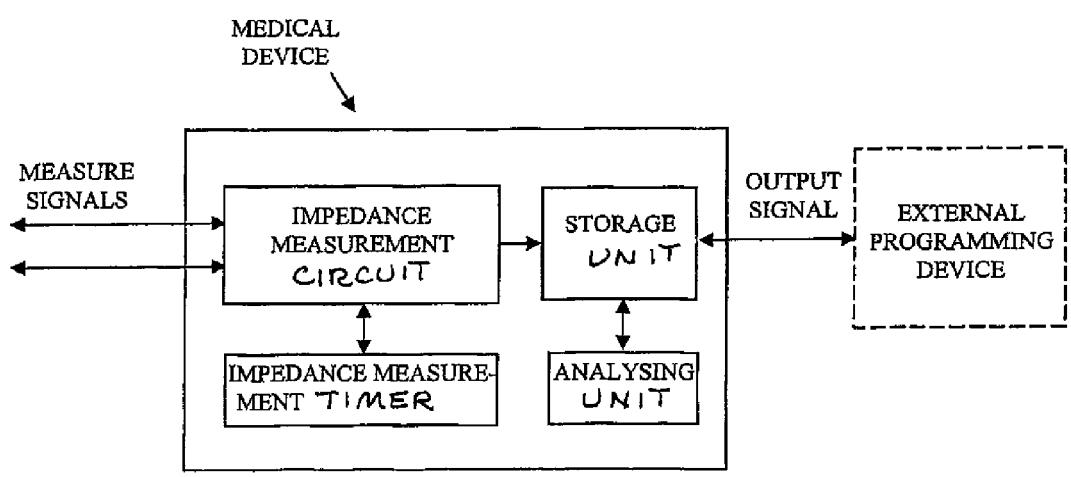
FIG. 3 is a block diagram illustrating a medical device according to the present invention.

With references in particular to FIG. 3 the medical device according to the present invention will now be described in detail. The medical device 2 has an impedance measurement circuit connected to at least two intracorporeal measurement electrodes 6,8,16 (see FIGS. 1 and 2) arranged to measure the impedance of a tissue object inside the body of a patient, the impedance measurement circuit is adapted to apply a measurement current/voltage signal to the electrodes to measure and calculate the impedance of the measurement tissue object 10, and to store the calculated impedance value in a storage unit. The stored impedance values are used, by an analysis unit, to calculate the amount of visceral fat of the tissue object. The analysis unit e.g. arranged to determine the long term variation of the stored impedance values in order to obtain changes of the visceral fat of the tissue object. The impedance measurement is preferably performed automatically and on a regular basis under control of an impedance measurement timer.

According to a preferred embodiment of the present invention the calculated impedance is the DC impedance.

The measurement current/voltage signal has an amplitude of 1 µA-1 mA or 0.5 mV-0.5 V.

Figures 1, 2:
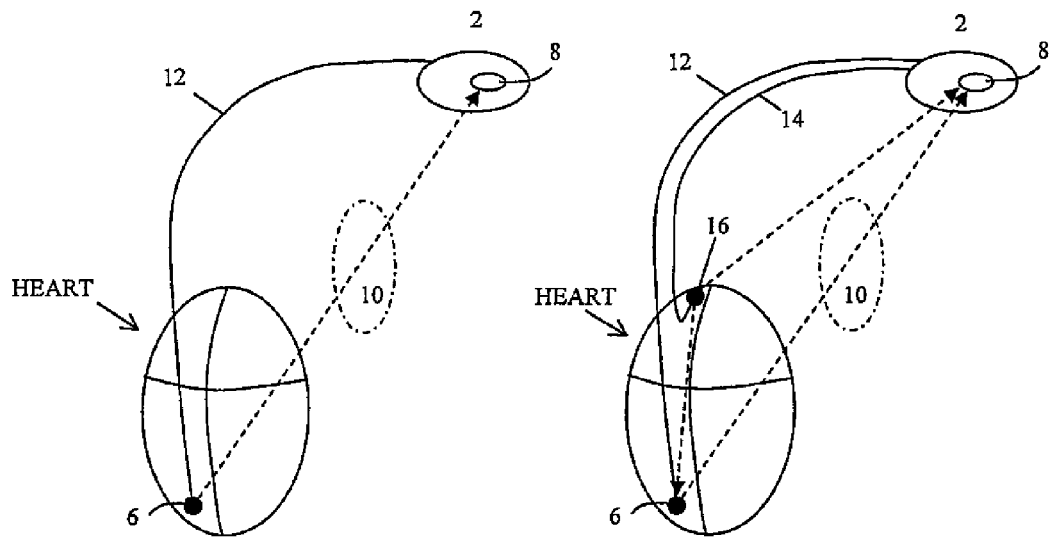
FIG. 1 is a schematic illustration of a measurement electrode configuration according to a first preferred embodiment of the present invention.
FIG. 2 is a schematic illustration of a measurement electrode configuration according to a second preferred embodiment of the present invention.

The measurement may be performed by a differential measurement electrode configuration, comprising at least three measurement electrodes adapted to be configured to perform measurements of different objects. Differential impedance measurements are performed by an electrode configuration where the measurement electrodes are arranged to cover different parts of tissue to be measured, i.e. in different directions for obtaining corresponding measurement vectors. If changes are indicated in the longer term, i.e. the changes for the respective impedance values are different, it may be an indication of increased amount of visceral fat. This is schematically illustrated in FIG. 2. The differential measurement electrode configuration may include one configuration where the resulting impedance is essentially not influenced by visceral fat. The calculated impedance values from measurements from the different configurations are compared to each other.

According to a preferred embodiment of the present invention the medical device is an implantable heart stimulator. Advantageously the electrodes used in connection with heart stimulation are used when performing the impedance measurements.

In a conventional single chamber system (see FIG. 1) an electrode lead 12 is arranged in the right atrium or right ventricle. It is then possible to perform impedance measurement between the tip electrode 6 (or ring electrode of a bipolar lead) at the distal end of the lead and the indifferent electrode 8 at the pacemaker housing. The measurement vector between the measurement electrodes may then cover tissue object 10 to be measured with regard to the visceral fat.

In a conventional dual chamber system (see FIG. 2) electrode leads 12, 14 are arranged in the right atrium and right ventricle, respectively. It would then be possible to perform differential measurements, i.e. to achieve to different measurement vectors between the respective electrodes 6, 16 at the distal ends of the leads and the indifferent electrode 8 at the pacemaker housing, or between the electrodes at the distal ends. In FIGS. 1 and 2 the measurement signals are indicated by dashed lines.

The present invention is naturally also applicable in left chamber systems (or in four chamber systems) where the electrode(s) is(are) arranged in the cardiac veins or in the coronary sinus.

According to another preferred embodiment of the present invention the calculated impedance is the AC impedance. The applied measurement signal has preferably a frequency in the interval of 1 kHz-10 MHz.

AC-impedance measurements normally require more energy.

As discussed above the complex impedance may be determined as well as the corresponding phase angle, which are used by the analysis unit for further analysis.

As with DC impedance measurements a differential measurement electrode configuration as discussed above may also be used when performing AC impedance measurements, and all different configurations discussed above in relation to DC impedance measurements are equally applicable for AC impedance measurements.

In a differential electrode configuration the measurement may be performed by applying measurement signals having different frequencies for the respective measurement electrode pair. Different frequencies may also be applied when only one measurement electrode pair is used, in that case the signals preferably may be alternatively applied.

The analysis unit preferably includes a predicting unit to predict trends based upon historical impedance values, and also a notifying unit adapted to notify the patient (or physician) if predetermined criteria are fulfilled regarding the changes of the impedance values indicating increased visceral fat. These predetermined criteria may be that the amount of visceral fat has increased with e.g. 10% since the last measurement was performed, e.g. one month ago.

As an alternative, the analysis unit, with a predicting means and a notifying unit, may be arranged in external programming device. The stored impedance values are then communicated, at a follow-up procedure, to the external programming device by use of conventional telemetry used in connection with implanted devices.

As previously mentioned the medical device preferably is an implantable heart stimulator. However, the present invention is applicable to any implantable device provided with electrodes arranged in relation to a tissue object, inside the body, of interest to measure and determine the amount of visceral fat.

It is beneficial to conduct the impedance measurements under the same conditions each time, in that the impedance level may vary in dependence of the posture of the patient. Therefore an input may be used from either an activity sensor or a heart rate monitor, calibrated for the patient in question. If an activity sensor is present, make sure that the patient is lying still, and has been for the last e.g. 30 minutes. If no activity sensor is present—monitor the heart rate and make sure it stays around +1-10% of the rest pulse for 30 minutes.

Although modifications and changes may be suggested by those skilled in the art, it is the intention of the inventor to embody within the patent warranted heron all changes and modifications as reasonably and properly come within the scope of his contribution to the art.

I claim as my invention:

1. A medical device comprising:
    an impedance measurement circuit comprising at least three measurement electrodes, configured to interact in vivo with intracorporeal tissue of a patient said at least three measurement electrodes of said impedance measurement circuit being configurable into at least two different measurement electrode configurations;
    said impedance measurement circuit being configured to apply a measurement signal, selected from the group consisting of a measurement current and a measurement voltage, to each of said at least two different electrode configurations and to measure and calculate an impedance of the tissue therefrom, impedance measurement circuit being configured to measure said impedance of said tissue using each of said at least two different measurement electrode configurations and to calculate said impedance values from respective impedance measurements obtained with said at least three measurement electrodes in said at least two different measurement electrode configurations, respectively;
    a storage unit connected to said impedance measurement circuit in which a plurality of respective impedance values, respectively representing impedance measured over time by said impedance measurement circuit, are stored; and
    an analyzing unit, having access to said storage unit configured to calculate an amount of visceral fat in said tissue by comparing the respective impedance measurements obtained with said at least two electrode configurations to each other, wherein said at least two different measurement electrode configurations include one configuration wherein the impedance is essentially not influenced by visceral fat of said tissue.

2. A medical device as claimed in claim 1 wherein said analyzing unit is configured to determine a long term variation of said impedance values stored in said storage unit to identify changes of the visceral fat of the tissue.

3. A medical device as claimed in claim 1 comprising a timer that operates said impedance measurement circuit to cause said impedance measurement circuit to measure said impedance automatically and at regular time intervals.

4. A medical device as claimed in claim 1 wherein said impedance measurement circuit is configured to calculate a DC impedance as said impedance of said tissue.

5. A medical device as claimed in claim 1 wherein said impedance measurement circuit is configured to measure AC impedance of said tissue as said impedance.

6. A medical device as claimed in claim 5 wherein said impedance measurement circuit is configured to apply two measurement signals respectively having different frequencies.

7. A medical device as claimed in claim 6 wherein said storage unit stores said impedance values each as formed by a complex impedance value having a phase angle, and wherein said analyzing unit is configured to analyze said complex impedance values and to calculate said amount of visceral fat in said tissue using said phase angles.

8. A medical device as claimed in claim 1 wherein said analyzing unit comprises a predicting unit configured to predict trends of said visceral fat based on historical impedance values stored in said storage unit.

9. A medical device as claimed in claim 8 comprising an intracorporeal unit containing said impedance measurement circuit and said storage unit, and an extracorporeal unit containing said analyzing unit and said predicting unit, and wherein each of said intracorporeal unit and said extracorporeal unit contains circuitry configured to establish a communication link allowing communication at least between said storage unit and said analyzing unit.

10. A medical device as claimed in claim 1 comprising a notifying unit configured to generate a humanly-perceptible notification if said analysis unit determines an increase in said visceral fat of said tissue.

11. A medical device as claimed in claim 10 comprising an intracorporeal unit containing said impedance measurement circuit and said storage unit, and an extracorporeal unit containing said analysis unit and said notifying unit, and wherein each of said intracorporeal unit and said extracorporeal unit contains circuitry to establish a communication link allowing communication at least between said storage unit and said analysis unit.

12. A medical device as claimed in claim 1 comprising an in vivo cardiac stimulator configured to apply electrical stimulation to the heart of the patient.

13. A medical device comprising:
    an impedance measurement circuit comprising a plurality of measurement electrodes, configured to interact in vivo with intracorporeal tissue of a patient, said plurality of electrodes of said impedance measurement circuit being configurable into at least a first measurement electrode configuration that is influenced by visceral fat of said tissue and a second measurement electrode configuration that is not influenced by said visceral fat of said tissue;

said impedance measurement circuit being configured to apply a measurement signal to said electrodes in each of said first and second different measurement electrode configurations based on the applied measurement signal to the electrode in each of said first and second different measurement electrode configurations, and to measure and calculate a first impedance value with said electrodes in said first measurement electrode configuration and to measure and calculate a second impedance value with said electrodes in said second measurement electrode configuration;

a storage unit connected to said impedance measurement circuit in which at least said first and second impedance values are stored; and an analyzing unit, having access to said storage unit, configured to calculate an amount of visceral fat in said tissue by comparing the first impedance value with the second impedance value to obtain a comparison result indicative of said amount of visceral fat in said tissue.

\* \* \* \* \*